United States Patent [19]

Krauter

[11] Patent Number: 5,191,879
[45] Date of Patent: Mar. 9, 1993

[54] VARIABLE FOCUS CAMERA FOR BORESCOPE OR ENDOSCOPE

[75] Inventor: Allan I. Krauter, Syracuse, N.Y.

[73] Assignee: Welch Allyn, Inc., Skaneateles Falls, N.Y.

[21] Appl. No.: 735,269

[22] Filed: Jul. 24, 1991

[51] Int. Cl.$^5$ ............................................. A61B 1/04
[52] U.S. Cl. ........................................ 128/4; 359/823; 359/826; 92/92
[58] Field of Search ..................... 128/4; 359/823, 824, 359/826; 92/92; 138/120

[56] References Cited

U.S. PATENT DOCUMENTS 4,620,769 11/1986 Tsuno.
4,777,524 10/1988 Nakajima et al. ................... 128/4 X
4,794,912 1/1989 Lia ................................... 92/92 X Primary Examiner—Vincent Millin
Assistant Examiner—J. Doyle
Attorney, Agent, or Firm—Wall and Roehrig

[57] ABSTRACT

A variable focus camera system for a borescope or endoscope has a camera or imager disposed within an imager sleeve and a braid and bladder assembly attached between the distal end of the imager sleeve and a lens assembly. A controlled pressure is applied through a pressure conduit into a confined volume defined by the imager sleeve, the braid and bladder assembly, and the lens assembly. The braid and bladder assembly expands axially but not radially, when pressure is applied, and changes the relative position of the imager and lens between a far focus and a near focus position.

10 Claims, 4 Drawing Sheets

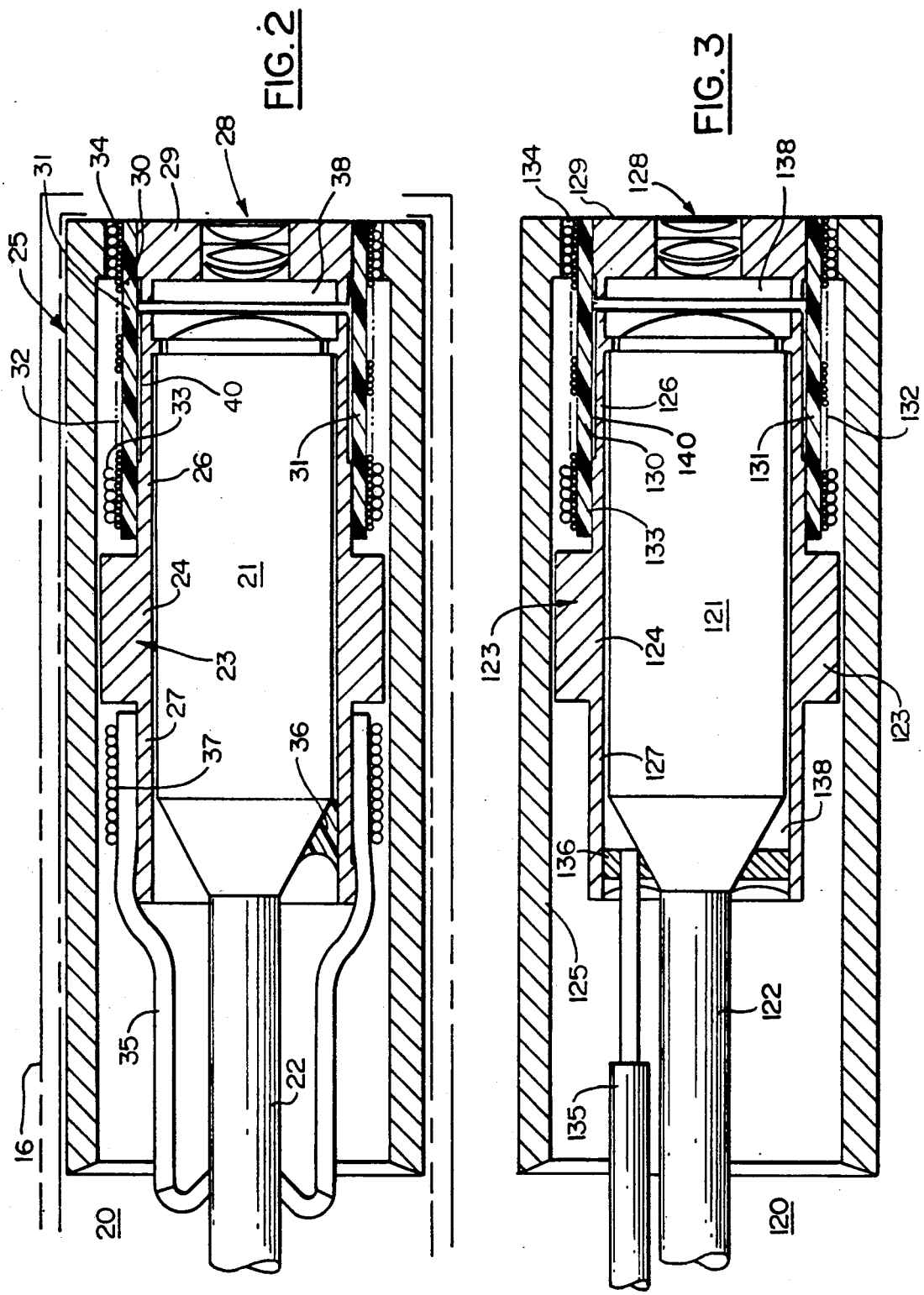

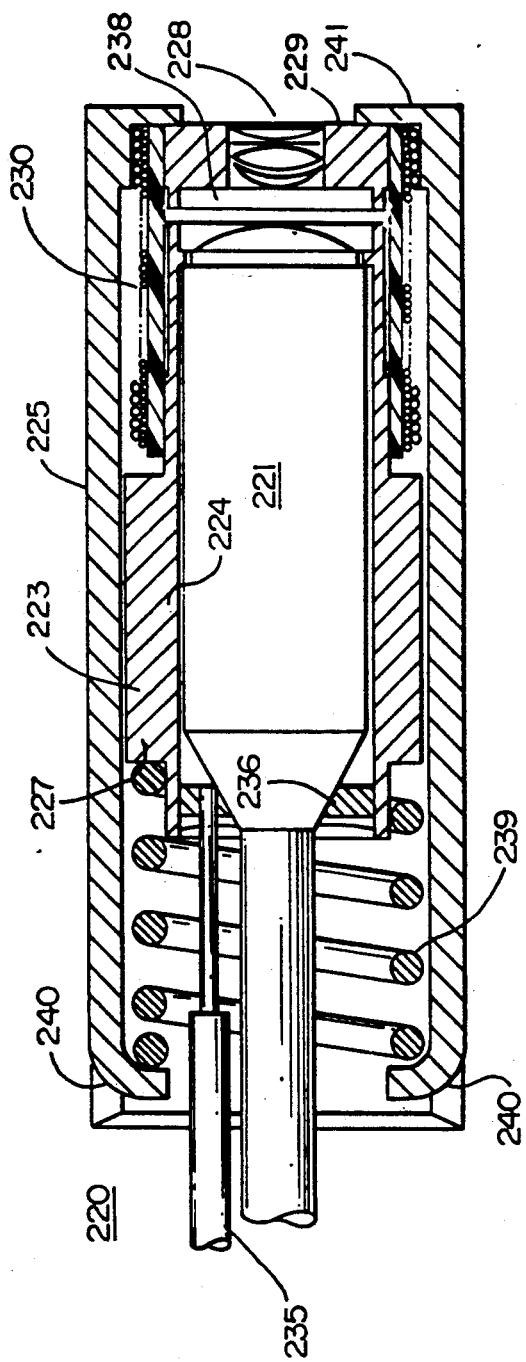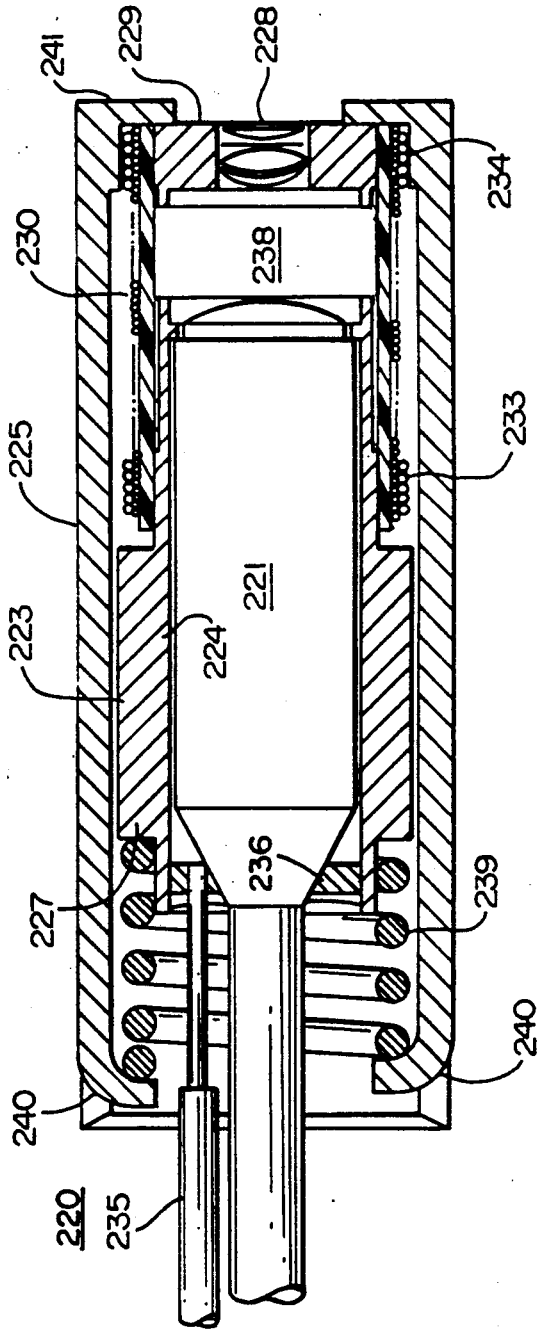

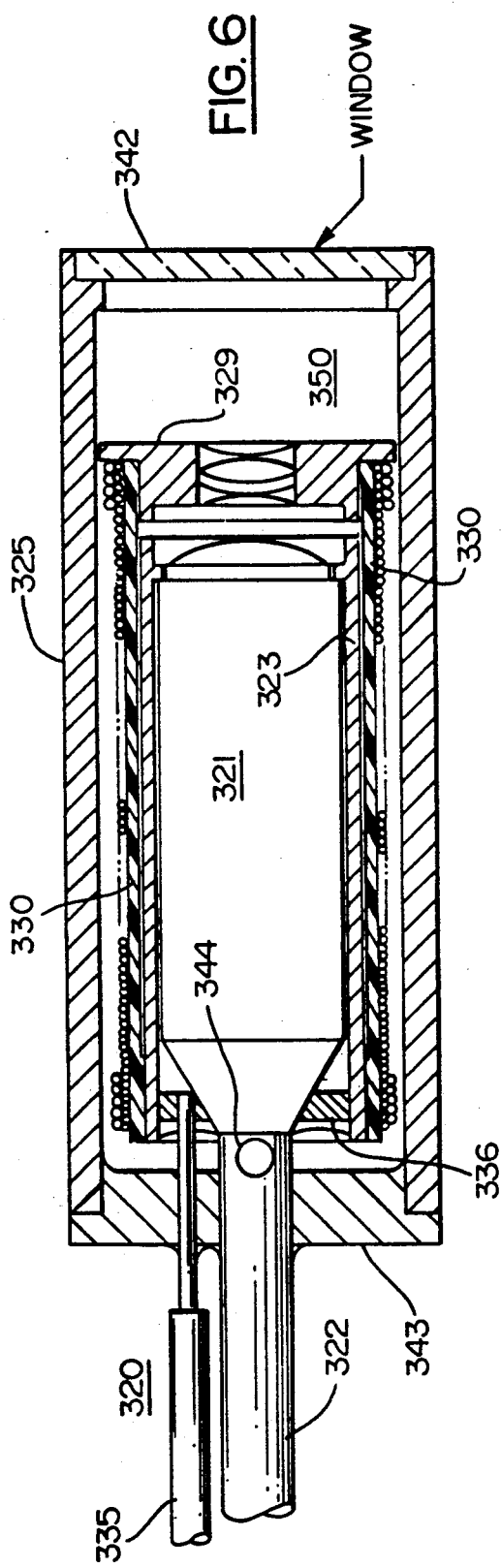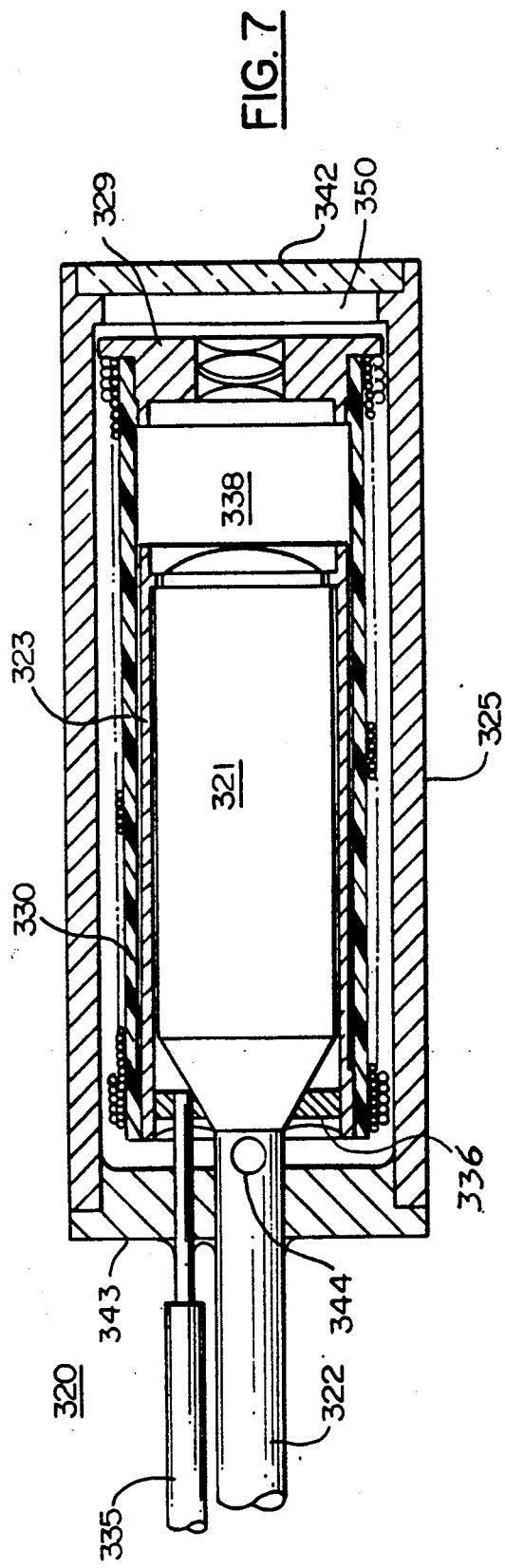

VARIABLE FOCUS CAMERA FOR BORESCOPE OR ENDOSCOPE

BACKGROUND OF THE INVENTION

This invention relates to devices that respond to fluid pressure, and is more specifically concerned with an elongated flexible probe having hydraulic or pneumatic focusing in its imager or camera section.

A borescope, endoscope, or similar flexible probe can be generally configured as an elongated flexible insertion tube with a viewing head at its distal or forward end and a control housing for controlling or steering the distal or forward end. The typical borescope has a bendable tubular steering section or articulation section at the distal end adjacent the viewing head. The viewing head, which can be optical i.e. (fiber optic) or video (e.g., a CCD imager), can be situated in the distal fitting of the bending neck. A signal conduit or bundle, which can be a wire bundle in the case of a video device or a fiber optic bundle in the case of an optical device, passes from the head through the insertion tube exiting to a suitable viewing device. A fiber optic bundle is also used to carry illumination to the viewing head for illuminating a target in an enclosed area.

The camera in a video borescope or endoscope typically has a fixed-focus lens assembly with a small aperture so as to have a large depth of field. Because of the small lens aperture, the required illumination has to be rather strong, and especially so when a color image is to be presented.

While focusing systems are theoretically possible, no one has previously proposed a highly reliable yet simple system which could be incorporated into a small-diameter probe.

A bellows-type arrangement for moving the objective lens of an optical type borescope or endoscope is shown in U.S. Pat. No. 4,620,769. Pressure is supplied through a small tube to a bellows unit to move a lens. The bellows expands or contracts in accordance with the applied pressure. Oil is used as a working fluid.

U.S. Pat. No. 4,794,912 describes a braid-and-bladder pneumatic or hydraulic "muscle," i.e., linear traction motor. The purpose of that motor is to articulate or bend a portion of the probe just proximal to the viewing head.

OBJECTS AND SUMMARY OF THE INVENTION

It is an object of this invention to provide a straightforward remote focusing system for a probe which has a distally located video camera or other imager.

It is an object to provide a focusing system to move the lens cell relative to the imager under either manual or automatic control.

It is a further object to provide a focusing system so that larger lens apertures can be employed, permitting imaging under ambient or low supplemental illumination.

It is another object to provide crisp focus on the imager from any object at any distance from the probe.

According to an aspect of this invention, a borescope or endoscope has a variable focus camera contained at a distal head of a flexible, elongated insertion tube. The camera includes a variable focus assembly that can move the imager proximally or distally with respect to the lens cell. The latter can be affixed at the distal end of the head. In one preferred embodiment the imager is mounted within an imager sleeve that slides axially within a head sleeve. The imager sleeve and lens cell holder are joined by a bladder assembly formed of an elastomeric tube and a braid disposed over the tube. Here, the braid is formed of more or less inextensible filaments (i.e., stainless steel wires). The braid has a high braid angle measured relative to the axis of the tube, i.e., substantially greater than 54.7°, preferably close to 90°. Monofilament wraps secure the bladder and braid to the lens cell holder and to the imager sleeve. The braid, having both right-and left-hand windings, maintains its orientation relative to the probe, so that the display is properly oriented. The large braid angle permits the elastomeric tube bladder to expand axially, but restrains its growth radially. The imager sleeve is sealed and a pressure conduit extends to the confined volume defined by the imager, imager sleeve, the bladder assembly and the lens holder.

Normally the imager sleeve and imager are biased distally to a far-focus position with respect to the lens cell. Air pressure applied through the conduit into the said confined volume causes the bladder assembly to expand axially, and to push the imager and imager sleeve proximally to a near focus position. Air pressure can be controlled manually, and focus can be judged from the image presented on a viewing screen. Alternatively, focusing can be automatically adjusted, for example employing a high-frequency band pass technique.

Only a small axial movement is necessary to effect the desired focus variation. This small amount of movement is accommodated within the head sleeve, and wire or cable leads and the focus pressure conduit move proximally or distally within the insertion tube.

In some embodiments the focusing pressure conduit can surround the video wire leads. In alternative embodiments, a separate focus pressure tube extends within the insertion tube and communicates with the confined volume inside the imager sleeve. Here a smaller diameter focus pressure tube that is not coaxial with the video leads can be used.

In other embodiments, the lens cell can be moved by the bladder assembly, with the imager and imager tube being held fixed within the head tube.

The invention applies not only to video type cameras, in which a video signal is generated and is carried on a conductor channel, but also to fiber type imagers, in which the image is formed directly onto a fiber bundle and is carried on the fiber optic bundle to a viewer or display device.

The invention can also be employed in a rigid probe device as well as in a flexible borescope or endoscope.

The above and many other objects, features, and advantages of this invention will present themselves to those skilled in the art from the ensuing description of several preferred embodiments, when read in conjunction with the accompanying Drawing:

BRIEF DESCRIPTION OF THE DRAWING

FIG. 2 is a sectional view of a variable focus viewing head according to one embodiment of this invention.

FIG. 3 is a sectional view of a variable focus viewing head according to another embodiment of this invention.

FIG. 4 is a sectional view of a variable focus viewing head according to a further embodiment, shown in a far focus position.

FIG. 5 is a sectional view of this embodiment shown in a near-focus position.

FIG. 6 is a sectional view of another embodiment shown in a far-focus position.

FIG. 7 is a sectional view of another embodiment shown in a near-focus position.

DETAILED DESCRIPTION OF A PREFERRED EMBODIMENT

Figure 1:
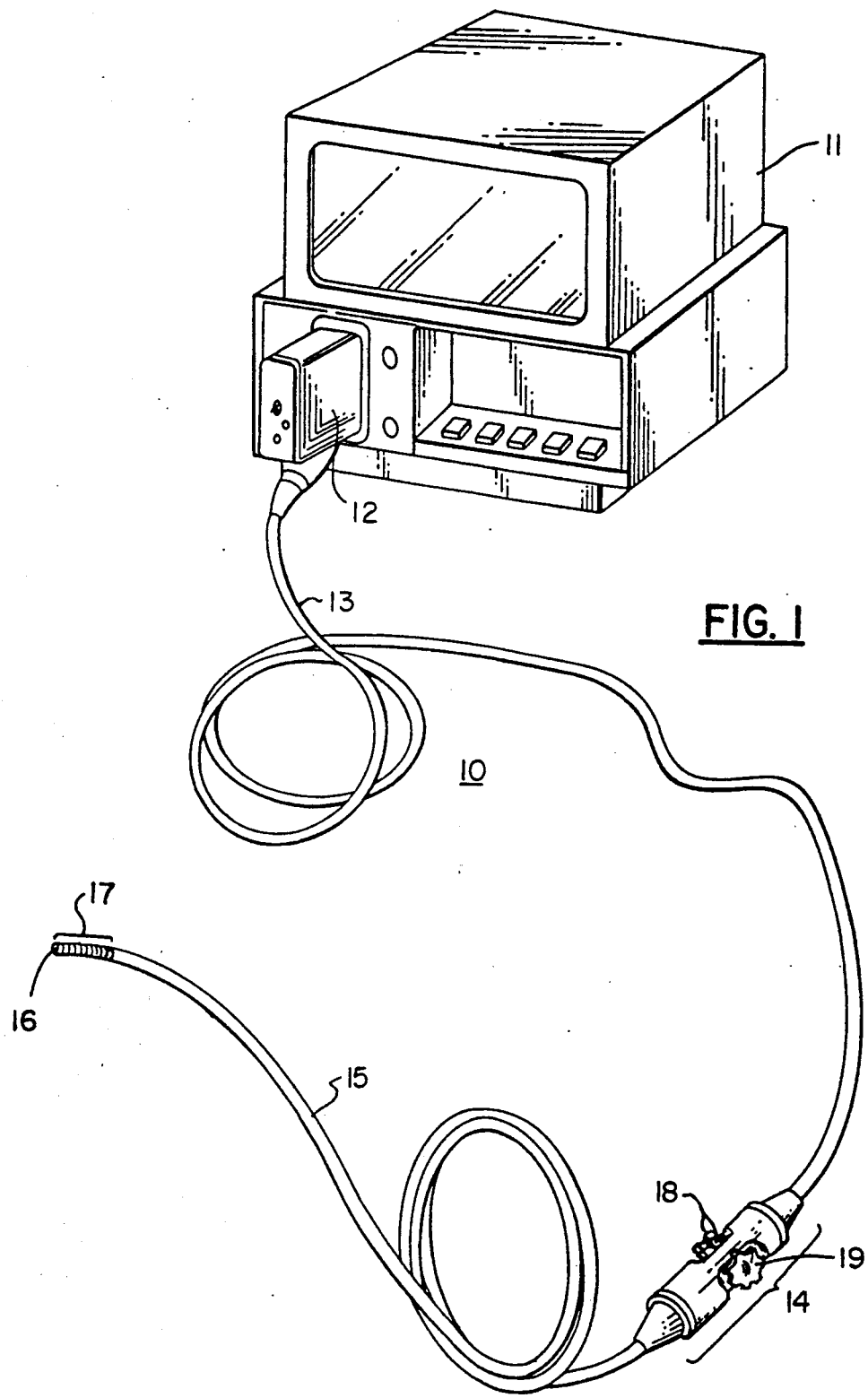
FIG. 1 is a perspective view of a borescope assembly in which the focusing system of this invention is incorporated.

With reference to the Drawing, FIG. 1 shows a video borescope system 10 having a video monitor and console 11 with a connector adapter 12 that connects the console to an umbilical or power tube 13 leading to a borescope steering control unit 14. An elongated flexible insertion tube 15 extends distally from the control unit 14, and has a video probe head 16 at its tip with a bending or steering section 17 connecting the flexible insertion tube 15 to the head 16. Steering knobs 18 on the control unit 14 rotate to control up and down articulation and left and right articulation of the bending section 17, either by means of steering cables within the sheath of the insertion tube 15 or by pneumatic steering using fluid dynamic muscles of the type described in U.S. Pat. No. 4,794,912. A focusing knob 19 on the control unit actuates a variable pressure regulator to apply a controlled pressure for focusing a variable focus video camera within the head 16. The construction of the variable focus camera assembly will next be described initially with reference to FIG. 2.

As shown in FIG. 2, a variable focus camera assembly 20 disposed within the viewing head 16 of the borescope insertion tube 15. The camera assembly has a CCD-based video camera or imager 21 from which video leads or wires 22 extend proximally. These leads 22 carry the video signal of an object being viewed by the camera. The camera 21 is affixed within an imager sleeve 23. The latter is generally tubular with an annular land 24 that slidably contacts an inner surface of a tubular head sleeve 25. The head sleeve 25 is affixed within the outer sheath of the viewing head 16.

The imager sleeve 23 has a distal portion 26 that is radially recessed below the land 24, and a proximal portion 27, also of smaller diameter than the land 24, that extends proximally. A focusing lens ell 28 is disposed within a lens holder 29, the latter being affixed onto a distal end of the head sleeve 25.

An axially expandable bladder assembly 30 fits over the imager sleeve distal portion 26 and a tubular protrusion on the lens holder 29. This bladder assembly 30 is comprised of an inner elastomeric tube 31 within a tubular braid 32. In this case, the inner elastomeric tube can be formed of a black urethane, which has a low reflectance to cut down glare between the lens cell 28 and the camera or imager 21. The braid 32 is formed of stainless steel filaments that lie at a high braid angle, i.e. at least 54.7° and preferably close to 90° with respect to the axial direction. A proximal wrap 33 and a distal wrap 34, each formed of a winding of monofilament or appropriate thread, hold the proximal and distal ends of the bladder assembly 30 onto the imager sleeve distal portion 26 and onto the lens holder 29, respectively.

In this embodiment a pressure conduit or tube 35 surrounds the video leads 22 from the imager. Controlled air pressure is supplied through this conduit 35 to vary the focus of the camera assembly 20. A plug of epoxy 36 or other suitable compound anchors the imager 21 in the imager sleeve 23. In this case, the plug 36 must not be air tight. Instead, a seal is formed by wraps 37 to seal the conduit 35 onto the proximal portion 27 of the imager sleeve. Here, the wraps 37 seal the controlled air pressure within a volume that is defined by the imager 21, imager sleeve 23, the lens holder 29, and the bladder assembly 30.

A controlled air pressure is supplied from the control unit 14, through the pressure conduit 35 which runs the length of the insertion tube 15, to the imager sleeve 23. Controlled air pressure varies the focus of the camera assembly 20. This focus variation occurs as follows.

When a zero pressure level is supplied through the pressure conduit 35, the imager sleeve 23 is in contact with the lens holder 29. In this case, this contact is caused by the tension of the elastomeric tube 31 of the bladder assembly, and also by any axial compressive force from the video leads 22 and the pressure conduit 35. This is considered a far-focus position, and the optics are focused at or slightly beyond infinity. When controlled air pressure is supplied through the pressure conduit 35, air pressure increases inside the confined volume 38. This air pressure increase causes the bladder assembly 30 to expand axially. However, because of the large braid angle of the braid 32, the bladder assembly 30 cannot expand radially As a result, the combination of imager sleeve 23, imager 21, leads 22, and pressure conduit 35 moves proximally, i.e., away from the lens holder 29. The extent of this movement depends upon the applied pressure. This movement varies the focus of the lens cell 28 relative to the imager 21 such that a closer focus is produced at higher pressures.

Typically, only a small axial movement of the imager 21 is required for a wide range of focus lengths. This small movement of the imager, typically no greater than about 0.100 inches, is easily accommodated in the viewing head 16. The movement of the video leads 22 and the control pressure conduit 35 is easily accommodated over the length of the insertion tube 15.

The elongated distal portion 26 of the imager sleeve 23 contains a relief portion 40 for the bladder and braid assembly 30. This relief permits more axial expansion distance for the bladder assembly 30 than would be available only between the very distal end of the imager sleeve 23 and the proximal end of the lens holder 29. A large braid angle, i.e. close to 90°, was chosen to avoid having the braid 32 grow in diameter as pressure increases. The use of a high braid angle bladder assembly 30 also results in the no-pressure far focus, i.e., the optics are focused at infinity when there is no pressure applied. In an alternative arrangement, a pneumatic muscle braid configuration with a small braid angle below 54.7° could have been employed. In such case, the braid would increase in diameter and decrease in length with increasing pressure, and this would result in a zero-pressure near focus arrangement.

The braid angle of 54.7° is the theoretical demarcation between an axially elongating and an axially contracting braid-bladder combination. For a bladder having negligible stiffness, an increase in internal bladder pressure causes the combination to elongate when the braid angle exceeds 54.7° and to contract when the braid angle is below 54.7°.

An alternative embodiment of this invention is shown in FIG. 3, where similar features to those shown in FIG. 2 are identified with the same reference numbers, but raised by 100. In this case, the camera assembly 120 has a camera or imager 121 disposed within the imager sleeve 123, which, as with the previous embodiment has an annular land 124 that is in slidable contact with an inner surface of the head sleeve 125. A bladder and braid assembly 130 is attached at one end to the distal portion of the imager sleeve 123 and at its other end to the lens holder 129. In this case, a seal 136 formed at the proximal or back end of the imager sleeve 123 closes off a volume 138 within the imager 121, imager sleeve 123, bladder assembly 130 and lens holder 129. A small-diameter pressure conduit 135 is disposed outside of the video leads 122, rather than over them as in the previous embodiment. A distal end of the conduit 135 penetrates the seal 136 to apply a controlled pressure to the confined volume 138.

A third embodiment is shown in FIGS. 4 and 5, in which elements similar to those of the previous embodiments are identified with the same reference numbers, but raised by 200. This embodiment is similar to that of FIG. 3, but employs a biasing spring 239 whose distal end pushes against a shoulder 227 formed by the land 224 of the imager sleeve 223. Retaining tabs 240 in the head sleeve 225 are bent in to confine the proximal end of the spring 239. In equivalent embodiments a pin or other spring retaining means could be employed. The lens holder 229 is retained in the head sleeve 225 by a flange 241.

FIG. 4 shows the camera assembly 220 of this embodiment in a far focus arrangement, wherein no pressure is applied, and the braid and bladder assembly is collapsed axially. When compressed air is applied through the pressure conduit 235 into the confined volume 238 then the braid and bladder assembly 230 expands axially without radial growth, as shown in FIG. 5. The distal end of the imager 221 is moved away from the lens cell 228 and holder 229 to obtain a near focus condition, i.e. to bring into focus objects near or substantially adjacent the distal face of the borescope head 16.

A further embodiment 320 is illustrated in FIG. 6 and FIG. 7 with corresponding parts being identified with the same reference numbers as in the previous embodiments, but raised by 300. In the remotely focusing camera assembly 320 of this embodiment, the camera or imager 321 and the associated imager sleeve 323 are held fixed within the head sleeve 325. The braid and bladder assembly 330 couples the imager sleeve 323 to a movable lens holder 329. Here, there is a separate window 342 at the distal end of the sleeve 325, and a wall 343 sealing off the proximal end thereof. The leads 322 and the pressure conduit 335 penetrate the proximal wall 343 and also penetrate through the seal 336 at the proximal end of the imager sleeve 323. As shown in FIG. 6, when there is no pressure applied through the pressure conduit 335, the elastomeric bladder and braid assembly 330 pulls the lens holder 329 proximally to a far focus position. When a controlled pressure is applied through the pressure conduit 335, the bladder and braid assembly 330 expands axially, and moves the lens holder 329 axially away from the imager 321, i.e. to a near focus position as shown in FIG. 7. A small clearance is provided between the radially outer edge of the lens holder 329 and the inner wall of the sleeve 325. Also, a vent 344 in the form of an aperture or slit is provided in a flexible sleeve that covers the leads 322. This vent provides an exit for air that would otherwise be contained in the sealed volume 350 inside sleeve 325 when the lens holder 329 moves distally. The vent also provides an entrance for air into the volume 350 when the lens cell moves proximally. The bladder and braid assembly 330 is attached with wraps of monofilament or appropriate thread at the proximal end of the imager sleeve 323 and at the lens holder 329, respectively.

Not shown in these embodiments is a fiber optic illumination cable for providing illumination of a target through the distal end of the viewing head 16. This illumination fiber optic bundle is provided in known fashion and, for example, at its distal end could fan out and be disposed between the head sleeve 25 and the sheath of the head 16.

As aforementioned, with the remote focusing camera of this invention, a much larger aperture lens can be employed than with the fixed-focus imagers of the prior art. For example, a conventional video camera employs a small aperture lens, typically no greater then 0.5 mm, which produces an f-number greater than f/4, to obtain a relatively large depth of field. However, with a variable focus camera, a much larger aperture can be employed, i.e., 1.0 mm or larger which produces an f-number less than f/3.

While the stroke of the variable focusing arrangement depends on the optical systems employed, for a borescope or endoscope, the maximum stroke required will not exceed about 0.100 inches.

Also, the compressed gas that is employed for moving the variable focus camera assembly should be quite clean, and typically is obtained through a high efficiency filter to avoid injecting any dust or other particles into the otherwise sealed optical system.

While the invention has been described in detail with respect to a few selected preferred embodiments, it should be understood that the invention is not limited to those precise embodiments. Rather, many modifications and variations would preset themselves to those skilled in the art without departing from the scope and spirit of this invention, as defined in the appended claims.

What is claimed is:

1. A remotely focusing camera assembly for a borescope or endoscope of the type wherein an elongated insertion tube has a distal head which contains an imager, the insertion tube having an image-carrying cable extending proximally from the image within the insertion tube to a viewing device for displaying an image of an object in the field of view of the imager, the camera assembly comprising:

a tubular head sleeve at the distal head of said insertion tube, a lens assembly including a focusing lens set and a tubular lens holder mounting same disposed at a distal end of the head sleeve;

an imager sleeve within the head sleeve, the imager sleeve containing the imager fixedly mounted therewithin;

with one of said lens assembly and said imager sleeve being fixedly mounted within the head sleeve, and the other thereof being axially slidable within said head sleeve;

means sealing the proximal end of said imager sleeve;

an elongatable braid and bladder assembly mounted onto a portion of said imager sleeve and said lens assembly such that the lens assembly, the braid and bladder assembly, the imager, the imager sleeve, and said sealing means define a confined volume, said bladder assembly including an elastomeric tube affixed at its one end over the imager sleeve and at its other end over said tubular lens holder of the lens assembly, and a braid disposed over said elastomeric tube and having substantially inelastic filaments oriented at an angle relative to the axis of the tube that substantially exceeds 54.7 degrees; and means for applying a controlled pressure into said confined volume for controllably elongating said bladder assembly to move said imager sleeve relative to said lens assembly between a far-focus positioned and a near-focused position.

2. The camera assembly according to claim 1 wherein said imager sleeve is slidable within said head sleeve and includes an annular land for slidably contacting an inner wall of said head sleeve, and a sleeve relief of lesser outer diameter than said land projects distally therefrom.

3. The camera assembly according to claim 2 wherein said braid and bladder assembly further includes a proximal winding of a filament wrap binding said bladder assembly onto a proximal end of said sleeve relief.

4. The camera assembly according to claim 3 wherein said braid assembly further includes a distal winding of a filament wrap binding said bladder assembly onto said lens assembly.

5. The camera assembly according to claim 1 further comprising resilient biasing means disposed in said head sleeve between a proximal end of said imager sleeve and anchor means in the head sleeve to urge the imager sleeve distally towards its far-focus position.

6. The camera assembly according to claim 1 wherein said imager sleeve is fixedly mounted within said head sleeve and said lens assembly is slidably disposed within said head sleeve.

7. The camera assembly according to claim 6 wherein the head sleeve contains a distal optical window and a proximal wall that together form a confined volume containing said imager, said imager sleeve, said lens assembly, and said elongatable braid and bladder assembly.

8. The camera assembly according to claim 1 further comprising resilient means disposed in said head sleeve and coupled between said imager sleeve and said lens assembly for urging said lens assembly and said imager sleeve to the far-focus position when said controlled pressure is relieved.

9. The camera assembly according to claim 8 wherein said resilient means includes a compression spring for pushing said imager sleeve and said lens assembly to said far focus position.

10. A remotely focusing camera assembly for a borescope or endoscope which includes an insertion tube having a distal head that contains an imager, and an image-carrying cable extending proximally from the imager within the insertion tube to a viewing device for displaying an image of an object in the field of view of the imager, comprising:

a tubular head sleeve at the distal head of said insertion tube;

a lens assembly disposed at a distal end of the head sleeve;

an imager sleeve within the head sleeve, the imager sleeve containing the imager fixedly mounted therewithin;

with one of said lens assembly and said imager sleeve being fixedly mounted within the head sleeve, and the other thereof being axially slidable within said head sleeve;

means sealing the proximal end of said imager sleeve;

an elongatable braid and bladder assembly mounted onto a portion of said imager sleeve and said lens assembly such that the lens assembly, the braid and bladder assembly, the imager, the imager sleeve, and said sealing means define a confined volume, said bladder assembly including an elastomeric tube affixed at its ends to the imager sleeve and to the lens assembly, and a braid disposed over said elastomeric tube and having substantially inelastic filaments oriented at an angle relative to the axis of the tube that substantially exceeds 54.7 degrees; and means for applying a controlled pressure into said confined volume for controllably elongating said bladder assembly to move said imager sleeve relative to said lens assembly between a far-focus position and a near-focus position; wherein said imager sleeve is fixedly mounted within said head sleeve and said lens assembly is slidably disposed within said head sleeve, wherein the head sleeve contains a distal optical window and a proximal wall that together form a confined volume containing said imager, said imager sleeve, and said lens assembly, and said elongatable braid and bladder assembly, and wherein said image-carrying cable includes a sheathed image conduit extending from said imager proximally out of said imager sleeve and said head sleeve, and said conduit is provided with a vent in the region between the imager sleeve and the head sleeve.

* * * * *